United States Patent [19]
Deindoerfer et al.

[11] 3,999,948
[45] Dec. 28, 1976

[54] DIAGNOSTIC REAGENT HOLDER AND METHOD

[75] Inventors: Fred H. Deindoerfer, Los Angeles; Roland Jang, Saratoga; H. Theodore Rudow, Atherton, all of Calif.

[73] Assignee: International Diagnostic Technology, Santa Clara, Calif.

[22] Filed: Nov. 3, 1975

[21] Appl. No.: 627,941

[52] U.S. Cl. ............................ 23/230 B; 23/253 R; 23/253 TP; 23/259; 128/2 W; 195/103.5 R; 195/127; 356/244; 356/246

[51] Int. Cl.² .................. G01N 1/00; G01N 21/24; G01N 33/16

[58] Field of Search ............. 23/259, 230 B, 253 R, 23/253 TP; 356/244, 246; 128/2 W; 195/127, 103.5, 63

[56] References Cited

UNITED STATES PATENTS

| | | | |
|---|---|---|---|
| 2,749,797 | 6/1956 | Harks | 356/246 |
| 3,443,903 | 5/1969 | Haack et al. | 23/253 TP |
| 3,507,269 | 4/1970 | Berry | 23/253 TP X |
| 3,526,480 | 9/1970 | Findl et al. | 23/253 TP |
| 3,881,993 | 5/1975 | Freake et al. | 195/127 X |
| 3,901,657 | 8/1975 | Lightfoot | 23/253 TP |
| 3,904,373 | 9/1975 | Harper | 23/253 TP |
| 3,907,503 | 9/1975 | Betts et al. | 23/253 R |

*Primary Examiner*—Robert M. Reese
*Attorney, Agent, or Firm*—Flehr, Hohbach, Test, Albritton & Herbert

[57] ABSTRACT

A diagnostic reagent holder specifically adapted for the detection of an unknown quantity of a biologically derived sample suitably by radioimmunoassay, fluorometric detection or by spectrophotometry. The holder comprises an elongate shaft with a support surface adjacent one end of the shaft. Diagnostic reagent is covalently attached to a self-supporting film such as a disc and firmly secured to the support. The diagnostic reagent, e.g., antibody, is stirred during incubation in contact with the sample to be detected, e.g., antigen, in solution. In a "sandwich" technique labelled substance (e.g., fluorochrome-labelled antibody) is reacted with the sample on the film followed by thorough washing. Then, the holder is slid into a novel viewing housing which precisely positions the film at a window for viewing as with a fluorometer. To avoid loss of labelled substance during handling, and especially during positioning in the viewing housing, one or more protective protrusions are provided around the periphery of the support surface.

21 Claims, 5 Drawing Figures

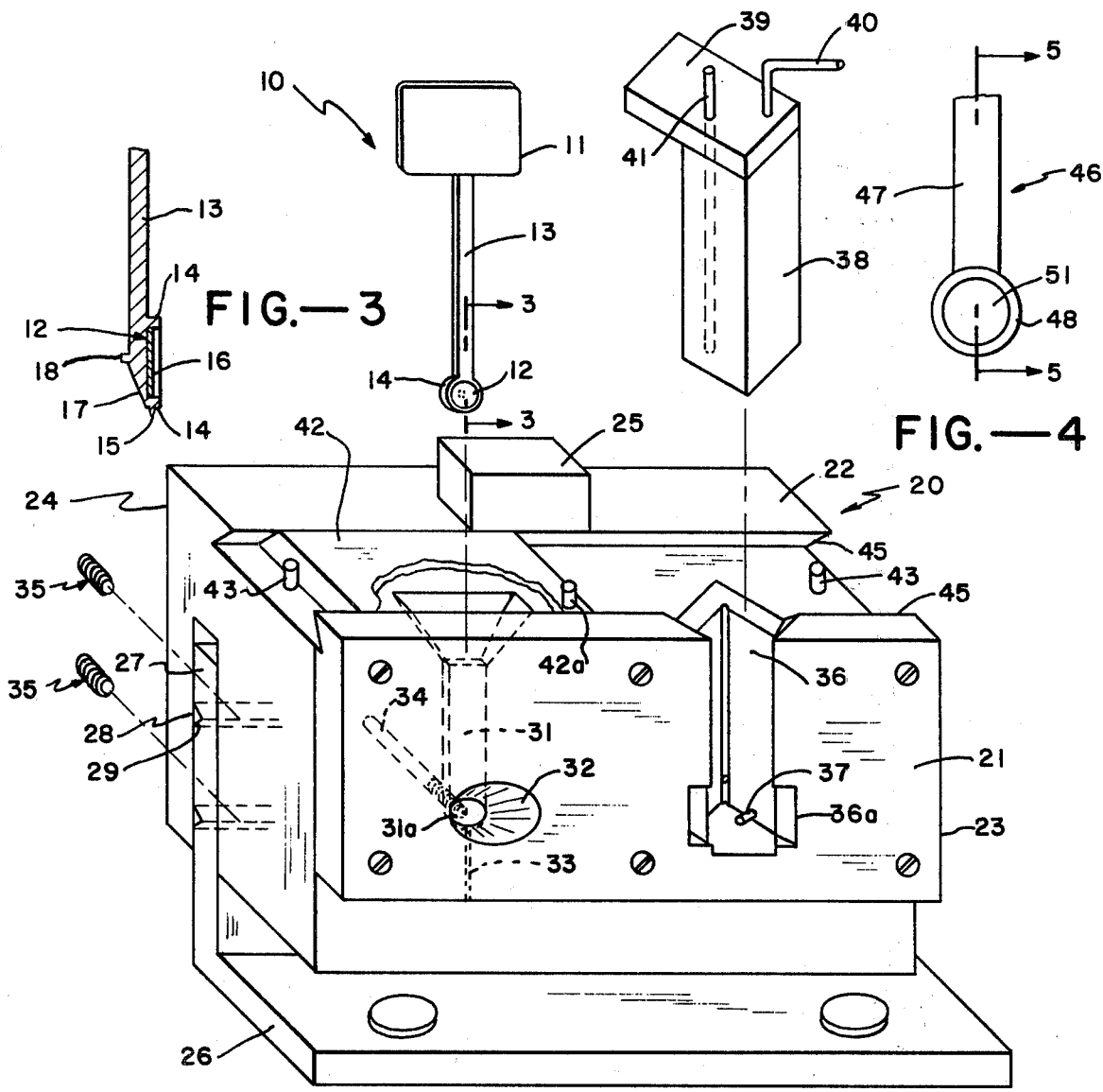
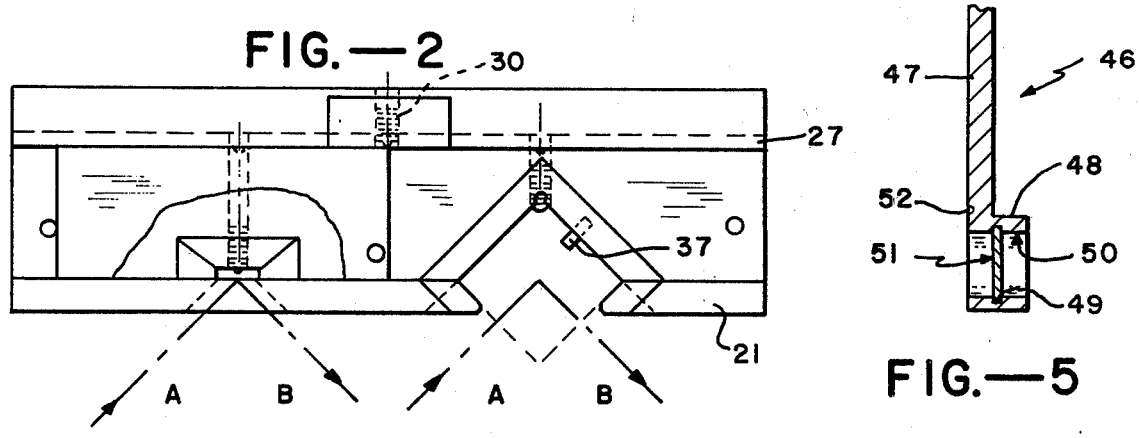

DIAGNOSTIC REAGENT HOLDER AND METHOD

CROSS-REFERENCE TO RELATED APPLICATION

Reference is made to application Ser. No. 553,582, filed Feb. 27, 1975, in the name of Richard A. Harte, entitled "Fluorometric System, Method and Test Article".

BACKGROUND OF THE INVENTION

There are many techniques available for the detection of an unknown quantity of a biologically derived sample (e.g., serum or urine). During such techniques, a labelled substance which has reacted with the sample must be separated from the unreacted labelled substances which includes free and non-specifically bound substance. This separation in liquid form is known to be inefficient, unreliable, and tedious. Many solutions have been proposed to solve this problem by the use of diagnostic reagents coated on a solid surface which combine with the labelled substance.

In one technique, reagents are coated upon plastic test tubes by physical adsorption of antibodies specific to the sample substance to be tested. See, e.g., articles by Catt et al. in the *Journal of Biochemistry*, 1966, Vol. 100, page 31c and in *Science*, Vol. 158, page 1570, 1967. This technique is difficult to control because of the non-uniformity of the plastic surface and imprecision in the coating technique. Furthermore, during washing to remove unreacted labelled substance, a relatively weak physical coating bond holding the antibodies can be disrupted resulting in their loss along with reacted labelled substance. Also, this technique requires a separate procedure for the coating of each test tube. This would be particularly time consuming, especially to insure reproducibility, if covalent attachment were employed to prevent the loss of diagnostic reagent. In addition, such test tube coating does not lend itself to the precise viewing required in a solid front surface fluorometric system. Furthermore, use of a test tube restricts covalent attachment to the material of construction used in making the tube.

Another solid surface approach is set forth in Bratu, Jr., et al. U.S. Pat. No. 3,826,619. This system employs a physically adsorbed diagnostic reagent coated on the tip of a holder. This tip is first fitted into a receptacle for the sample and then into a receptacle for the labelled substance. This system is subject to inaccuracies because of losses in rubbing of the unprotected tip against the close fitting receptacle. Also, there is no ability to stir the tip in the receptacle leading to long incubation periods. Additionally, this technique does not lend itself to reproducible mass production as each holder must be individually coated with diagnostic reagent. Furthermore, it is undesirable for precise viewing.

SUMMARY OF THE INVENTION AND OBJECTS

In accordance with the present invention, a diagnostic reagent holder is provided which is suitable for use in the labelled determination of an unknown quantity of a biologically derived sample. The holder includes an elongate shaft connected to mounting means adjacent one end of the shaft. A self-supporting film bearing a diagnostic reagent is firmly secured to the mounting means. In one embodiment, the mounting means comprises a support surface to which the film is firmly adhered. The diagnostic reagent is preferably covalently attached to a large number of discs formed of the film, simultaneously, in a separate operation. Then such discs are secured individually to such support. Protrusion means such as a protective rim is provided around the periphery of the film to prevent loss by abrasion of diagnostic reagent, labelled sample or substance which has reacted with the film. The holder is especially adapted for precise positioning in a viewing housing. A pivot portion projects from the holder to form a pivotal axis to facilitate stirring.

The viewing housing includes a slot means for positioning the disc surface adjacent a window of the same. Also, it may be mounted in a detection assembly such as in a fluorometric system for lateral movement along a track. The viewing housing includes multiple windows, one of which is used for viewing a cuvette in a liquid system. Others can include standards or blanks. The system is particularly adapted for fluorometry on a surface in that the disc is precisely positioned at an identical distance and angle with respect to both an excitation beam and a detector.

It is an object of the invention to provide a diagnostic reagent holder and method of use particularly adapted for the determination of a quantity of biologically derived sample.

It is a particular object of the invention to provide a holder and method of the foregoing type which is adapted for precise positioning in a viewing housing of a detection system.

It is another object of the invention to provide a holder and method of the foregoing type in which diagnostic reagent is attached to a film and thereafter placed on the holder to facilitate mass production.

It is another object of the invention to provide a viewing housing particularly adapted for precisely positioning the diagnostic reagent holder.

Further objects and features of the invention will be apparent from the following description of the preferred embodiments taken in conjunction with the accompanying drawings.

BRIEF DESCRIPTION OF THE DRAWINGS

FIG. 1 is an exploded perspective view of the viewing housing of the present invention illustrating a diagnostic reagent holder and cuvette above their respective slots.

FIG. 2 is a top view partially broken away of the holder of FIG. 1.

FIG. 3 is an expanded cross-sectional view of a portion of the diagnostic reagent holder of FIG. 1 taken along line 3—3.

FIG. 4 is a front view of a lower portion of another diagnostic reagent holder.

FIG. 5 is a cross-sectional view of the holder of FIG. 4 taken along line 5—5.

DETAILED DESCRIPTION OF THE PREFERRED EMBODIMENTS

Referring to the embodiments of FIGS. 1 and 3, a diagnostic reagent holder 10 is provided with a convenient handle 11 at one end and mounting means comprising support surface 12 toward the other end interconnected by an elongate shaft 13. Support surface 12 is on the front or viewing side of the holder. As illustrated, handle 11 is formed in an enlarged rectangulr shape of sufficient dimension transverse to shaft 13 for gripping either manually or by mechanical means. This permits convenient stirring of a liquid with the holder and provides support for a sample identification label. Other handle shapes may be employed for this purpose. Elongate shaft 13 serves to provide spacing between handle 11 and support surface 12 so that the holder may be stirred by gripping handle 11 above a solution while support surface 12 is in the solution. It facilitates rapid separation of solid and liquid phases. It also permits precise positioning of support surface 12 in a viewing housing as illustrated in FIG. 1 with the support surface positioned deeply within the housing to shield it from ambient light. The holder may be formed of any material relatively inert to the reactants such as moldable plastics.

A self-supporting film comprising disc 16 is firmly adhered to the front side of support surface 12 by a suitable adhesive material or plastic welding process. A diagnostic reagent is carried by disc 16, preferably by covalent attachment, as described in detail hereinafter. Support surface 12 and disc 16 are preferably of a circular shape to facilitate adhesion of the disc to the support surface without angular alignment.

Protrusion means comprising protective rim 14 surrounds a substantial portion of the periphery of support surface 12 and thus disc 16. In the illustrated embodiment, rim 14 extends around the entire periphery of the disc. Rim 14 projects a sufficient distance outwardly from the exposed surface of disc 16 normal to the support surface to protect the disc from loss of material bound thereto by abrasion. Other suitable protrusion means include a discontinuous rim with spaced elements or a number of circumferentially spaced points. Such protrusion means also includes the inner wall of a flat front surface of the holder which surrounds a recessed support surface. The outer surface of said protrusion means lies in a plane parallel to the face of disc 16 so that it may engage a cooperating surface of a housing of an optical instrument to precisely position disc 16 in the optical path.

A beveled edge 17 is provided on the lower end of the rear side of the holder to facilitate movement past a resiliently mounted projection for alignment in a slot of a viewing housing or the like.

A projection 18 is provided suitably also on the rear side of the holder opposite the center of the support surface to assist registry thereof with a corresponding housing recess. In another alternative embodiment, the holder may be beveled parallel to the shaft to register with a corresponding projection on the slot.

A pivot extension comprising pointed projection 15 extends from the holder at the film end or bottom to form a resting point. During stirring, the holder rests on point 15 in a liquid vessel, e.g., test tube, to facilitate circulation of fluid around the bottom.

Disc 16 bears a diagnostic reagent capable of reacting with a sample substance. For example, if the sample substance is an antigen, the diagnostic reagent may be an antibody specifically reactive with the antigen. Thus, the diagnostic reagent comprises one of a pair or more of reactive substances. The holder tyically is employed in the testing of body fluids, such as serum, urine or other fluids, to ascertain the presence of pathogens or their toxins or to ascertain concentrations of other substances in the fluid. The diagnostic reagent is a material which selectively or sterically fits with the mating sample substance. Sample substances include drugs of abuse, such as morphine, methadone, cocaine, and barbiturates; drugs used for the control of certain chronic diseases or conditions such as digoxin (cardiac disorders), insulin (digitalis), and diphenylhydantoin (epilepsy); hormones such as thyroxine and triiodothyroxine; steroid hormones such as aldosterone, cortisol, testosterone, estriol and progesterone; peptide and protein hormones such as adrenocorticotropin, angiotensin, gastrin, chorionic gonadotropin, follicle stimulating hormone, growth hormone, luteinizing hormone, neurophysin, placental lactogen, and thyroid stimulating hormones, vitamins such as cyanocobalamin and folic acid; enzymes such as chymotrypsin, creatine phosphokinase, alkaline phosphatase, and lactic dehydrogenase; antigens such as carcinoembyonic antigen, hepatitis associated antigen and alpha fetoprotein; antibodies such as anti-toxoplasmosis antibody, anti-thyroid antibodies and anti-nuclear antibodies; cellular formed bodies such as bacteria, fungi, protozoa, erthyocytes and leucocytes; serum proteins such as fibrogens, anti-hemophilic factors, lipoproteins, immunoglobulins and thyroxine binding globulin; cellular degradation products such as myoglobins, bacterial toxins, and lyzozymal digests, etc. Other substances can be employed so long as they are detectible or rendered so as by direct labelling or through binding with labelled specific binding proteins, substances, inhibitors, enzymes, antigens or antibodies, and can be attached to a surface, either before or after they are directly or indirectly labelled.

Disc 16 is formed of an essentially non-swellable, continuous, permeable material. As defined herein, an impermeable film is one which will not permit the passage of liquid from one side to the other during the present process. Although some penetration of liquid occurs, it is preferable that the film be sufficiently non-porous to prevent significant penetration. Use of this type of disc facilitates rapid washing of the surface after reaction with a labelled material to remove the background noise of unreacted labelled material. In contrast, permeable porous surfaces require extensive washing. In a preferred embodiment, the diagnostic reagent is covalently attached to the surface of disc 16. Thus, disc 16 may comprise substrates such as a polyacrylic polyamide, cellulosic or other polymeric film depending upon the diagnostic reagent to be employed.

The structural strength of the holder required during handling, especially stirring, is not required for disc 16. Conversely, the chemical properties desirable for disc 16, e.g., reactivity to form covalent attachments with diagnostic reagent is not necessary for holder 10. Thus, it is sometimes advantageous to form the disc and holder of different materials.

If disc 16 is formed of polymeric materials which does not include within its matrix groups reactive with the diagnostic reagent, such reactive groups may be coupled thereto by known chemical reactions. Groups of this type include amino groups, hydroxyl groups, mercapto groups, amido groups, and carboxyl groups. Suitable attachment of diagnostic reagents to polymers with such groups coupled to them are set forth in Bennich et al. U.S. Pat. No. 3,720,760.

Covalent attachment could be a time consuming difficult-to-reproduce operation in mass production if performed while disc 16 is secured to the support surface 12. It has been found desirable to first covalently attach the diagnostic reagent to a large number of the discs by agitating the same during reaction in a single vessel followed by adhering a disc to the support surface of each holder. It is important to note that handling of the discs without protection by protective rim 14 and without the ability to freely move the same by holder 10 is not a problem at this stage. Thus, abrasive contact with such discs to remove some diagnostic reagent would not result in inaccurate measurement procedures in carefully controlled manufacturing operations. The discs are placed on the support surface prior to reaction with the labelled substance and sample substance as set forth hereinafter. This protects the disc containing the sample and labelled substance from occasional abrasive contact which could result in the loss of signal detection and imprecision during analytical manipulations.

For simplicity of description, a typical fluorometrically labelled sandwich method will now be described.

In a first step, the diagnostic reagent (e.g., antibody) is covalently attached to the disc in a manner as set forth above. For mass production, it is convenient to form the discs by punching from a sheet of suitable material such as polyacrylic film. Then, the discs are grafted with a spacer arm or coupling reagent. A suitable reaction would include a large number of discs, e.g., 100 or more, in a stirred reaction vessel. Thereafter, the discs containing coupling reagents are reacted in a similar manner with a suitable antibody and washed and allowed to dry. Such discs are then secured to the support surface 12 as with a pressure sensitive adhesion.

In the following step, the holder is gripped by the handle to place the diagnostic reagent bearing disc into a solution of a fluid containing sample substance reactive with the diagnostic reagent, e.g., antigen. If present, the antigen reacts and combines with the antibody on the surface during an incubation period. It is advantageous to agitate the reactive substance during incubation. This provides a significantly faster reaction time. In addition, it has been found to increase the reproducibility of the experimental results, especially in short incubation periods. Handle 11 provides a convenient means for mechanically or manually stirring of the solution.

After incubation with the sample serum containing antigen, holder 10 is simply removed from the solution and washed with a suitable solvent such as aqueous phosphate buffer or distilled water.

In the following step, the labelled substance, suitably antibody labelled with a fluorochrome, radioactive substance, enzyme or phosphorescing substance, is contacted with disc 16 and incubated for a sufficient time to complete reaction between the labelled antibody and antigen. Again, it is advantageous to agitate the solution during incubation to decrease the reaction time and improve reproducibility of detection.

In the next step, the solution containing unbound labelled antibody is simply separated from the solid surface containing bound labelled antibody. Thereafter, the reacted solid surface is thoroughly washed to remove residual and non-specifically bound antibody which may remain on the disc. The efficiency of this washing step is extremely important in obtaining accurate results. Thus, the surface is thoroughly washed with a suitable rinsing solution such as aqueous phosphate buffer or distilled water. This illustrates the advantage of forming a firm covalent attachment of the diagnostic reagent with the disc to prevent its loss with labelled antibody bound to it during this step.

After washing, the holder 10 is transported to a detection system for quantitative measurement. In a particularly advantageous system, the label is a fluorochrome and the detection system is a fluorometric system of the type set forth in application Ser. No. 553,582, in the name of Richard A. Harte, entitled "Fluorometric System, Method and Test Article", filed Feb. 27, 1975. That system is incorporated at this point by reference.

A description follows of a viewing housing suitable for incorporation in the above fluorometric system or other detection systems and which is particularly adapted for precisely positioning of the above diagnostic reagent holder for optical detection.

Referring to FIGS. 1 and 2, a viewing housing 20 is illustrated which is particularly adapted for receiving diagnostic reagent holder 10 for viewing in a fluorometric system of the foregoing type. Viewing housing 20 includes front wall 21, top wall 22 and side walls 23 and 24. Housing 20 is slidably mounted onto an L-shaped base member 26 which, in turn, is mounted in a stationary position in a detection assembly. In the illustrated embodiment, housing 20 is provided with a longitudinal slot 27 extending parallel to front wall 21 along the entire length of the housing. Parallel detents 28 extending along the length of wall 27 are provided to mate with accomodating parallel grooves 29 in base 26. The cooperating detents and grooves form track means for sliding horizontal movement of the viewing housing.

Means are provided for limiting lateral movement along the track means to define at least two precise predetermined lateral index positions. Such means comprises pairs of ball spring type set screws 35 mounted on the rear side of the housing projection into slot 27. Screws 35 register with detents in the slot at such index positions. Pairs of spring mounted screws visible at the left side of the housing and also disposed at the right side are in registry with slot 27 to define a lateral path for the housing to ride upon. A station selector handle 25 is provided to facilitate movement of housing 20 between the different lateral stations along track means.

In the illustrated embodiment, the housing includes at least two viewing slots, one for viewing holder 10 and another for viewing a cuvette. In a fluorometric system, the viewing housing could be laterally moved so that the excitation and detector are rigidly mounted and housing 20 is moved into registry with the viewing slots. A third slot, not shown, may be included for viewing another holder with a zero or standard reading.

Means defining a slot 31 is provided with an upper opening through top wall 22. The lower end of slot 31 is in registry with an opening through front wall 21 forming a window 32 into the slot. Stop means is provided for limiting penetration of the reagent holder a predetermined distance along slot 31. In the illustrated embodiment, such stop means comprises the rounded lower portion 31a of slot 31. A scrap drain opening 33 communicating with the interior of slot 31 and projecting out of the housing is provided to prevent build-up of scraps which might accumulate after long-term use. In a fluorometric system as illustrated in FIG. 2, light from a source travels along path A and contacts the disc on the support surface through window 32 and the emitted light is received along path B by a fluorescence detector.

Setting means is provided to urge the reagent holder against a surface of slot 31 to provide a precise positioning of support surface 12 in the viewing housing when the holder contacts the stop means. In the illustrated embodiment, the setting means comprises a resiliently mounted projection in the form of spring mounted set screws 34 which projects toward front wall 21. Set screw 34 registers with projection 18 at the rear of holder 11 to precisely position support surface 12 in a predetermined fixed position adjacent window 32 with holder 10 in a viewing position.

Means defining a cuvette slot 36 is provided with an opening in front wall 21. Slot 36 is laterally spaced from slot 31 and includes a cuvette opening 36a of expanded area in comparison to the remainder of the slot. In the illustrated embodiment, the cuvette slot is of a square cross-section and is aligned in a 45° angle to front wall 21. Referring to FIG. 2, when viewing housing 20 is employed in a fluorometric system, excitation light is supplied along path A and is reflected along path B for detection at a 90° angle. The foregoing alignment facilitates this spacial relation. Stop means comprising stop pin 37 is provided for cuvette slot 36 to position the cuvette at a precise elevation. Alternatively, front surface fluorescence at other angles including 90° could also be measured using the system described in the aforementioned Harte patent application.

A fluid cuvette 38 of square cross-sectional area and transparent side walls fits precisely into cuvette slot 36. A top 39 is provided wtth an inlet tube 40 and an outlet tube 41 so that different diagnostic samples can be flowed into and out of the cuvette while it is in position.

Means is provided for sliding a light trap plate to cover whichever slot is not in use. Such means comprises a recess in top wall 22 together with parallel dove tail slots 45 at each end of the recess. A light trap plate 42 is slidably received in the recess and includes a pin 42a to facilitate movement and stop pins 43 to define the extent of movement.

In operation of the diagnostic holder portion of the viewing housing, holder 10 is inserted into slot 31 until disc 16 is precisely positioned adjacent window 32 by means of set screw 34 registering with projection 18 in the back of support surface 12. In the fluorometric system, excitation light travels along path A to excite fluorescence on the fluorescent labelled disc that is received along path B to find a suitable fluorometer detector in which the intensity of emission is measured. Alternatively, the above housing could be employed in other types of detection system such as radioimmunoassay using a Geiger counter, or in a spectrophotometer. If it is desired to analyze a fluid in cuvette 38, housing 20 is moved along its track laterally to align the cuvette with the detector.

The lower portion of another embodiment of the present diagnostic reagent holder is illustrated in FIGS. 4 and 5. Holder 46 includes a shaft 47 connected to mounting means comprising annular rim 48 with an internal retaining groove 49 extending the entire distance around the inner surface 50 of the rim. A self-supporting film 51 bearing diagnostic reagent is secured into retaining groove 49. By forming disc 51 of a flexible film, the larger diameter disc may be flexed to slide into registry with groove 49. Rim 48 also serves to protect disc 51 from abrasion. A recess 52 is provided on the back side of shaft 48 to assist registry with a cooperating set screw 34 of housing slot 31. Other recesses to assist registry include grooves in the holder adjacent the film and parallel to the shaft which align with corresponding projections in the sides of the viewing housing slot, e.g., of wedge shape. The remainder of holder 46 and the method of using it are the same as described with respect to holder 10.

In order to more clearly disclose the nature of the present invention, specific examples of the practice of the invention are hereinafter given. It should be understood, however, that this is done by way of example and is not intended to limit the scope of the invention.

EXAMPLE 1

1. Forming Covalent Bridges

Acrylic discs, ¼ inch in diameter, were punched from 6-mil thick polyacrylic acid film. The discs were uniformly grafted with an amine bridge using a carbodiimide catalyzed nucleophile substitution reaction. A typical reaction was carried out with stirring for two hours at room temperature using the following proportion of reactants:
100 discs
10 ml. of pH 6.0 sodium phosphate 0.1 M buffer
0.1 g. of 3,3′-Iminobispropylamine
0.05 g. of 1-cyclohexyl-3-(2-morpholineoethyl)-carbodiimide metho-p-toluenesulfonate After washing the discs, the amine bridge so formed was lengthened further by reaction with succinic anhydride, one end of which formed an amide linkage with the amine, the other end hydrolyzing to a carboxylic acid group on which protein can be immobilized. A typical reaction was carried out with stirring for thirty minutes at room temperature using the following proportion of reactants:
100 discs
10 ml. of distilled water maintained at pH 6.0–7.0 by dropwise addition of 10N. sodium hydroxide
0.1 g. of succinic anhydride added slowly over a 20 minute period 2. Covalent Attachment of Diagnostic Reagent After washing, the grafted discs were again reacted in a carbodiimide catalyzed reaction, this time with an antiserum. A typical reaction, under the same conditions as above, was carried out using the following proportion of reactants:
100 discs
10 ml. of pH 6.0 sodium phosphate 0.1M buffer
0.05 ml. of anti-human immunoglobulin G goat serum
0.05 g. of 1-cyclohexyl-3-(2-morpholineoethyl)-carbodiimide metho-p-toluenesulfonate 3. Securing to Holder After washing, the antibody containing discs were allowed to air dry at room temperature. Each of the support surfaces of diagnostic reagent holders of a type described herein were coated with one drop of an acrylic emulsion and allowed to dry to form a pressure sensitive adhesive. The discs were attached to said surfaces by careful placement followed by a gentle pressure on the disc topsides to secure them to the holders for use in subsequent assays.

4. Reaction with Sample Substance

Then one disc-containing reagent holder was inserted into a tube containing 0.5 ml. of a pH 7.4 sodium phosphate 0.01 M buffer solution including 1.0µl. of human serum, and agitated gently at room temperature for 30 minutes. The reagent holder was then removed and washed with buffer solution.

5. Reaction with Labelled Substance

After washing, the reagent holder was inserted into another tube containing 0.5 ml. of a pH 7.4 sodium phosphate of 0.01 M buffer solution including 5.0 µl. of a commercial solution of fluorescein isothiocyanate conjugated goat immunoglobulin G derived from anti-human immunoglobulin G goat serum, and agitated gently by mechanical stirring at room temperature for 30 minutes. The reagent was then removed and washed with buffer solution.

6. Measurement in Fluorometer

After washing, the reagent was placed into the fluorometer holder and its fluorescent signal determined. By comparison with fluorescent signals from known standard concentrations obtained similarly, as tabulated below, the sample concentration was found by interpolation to be 23 µg/ml. Correcting for its dilution (1:500), the original sample contained 11.5 mg/ml. of immunoglobulin G.

| Immunoglobulin G Concentration in Step 4 µg/ml. | Fluorescent Signal in Step 6 Arbitrary Units |
| --- | --- |
| blank | 50 |
| 1.1 | 72 |
| 28.5 | 357 |
| 56.9 | 763 |
| sample | 321 |

EXAMPLE 2

This example illustrates the importance of precise repeatable positioning of the diagnostic reagent holder with respect to the fluorometer.

Discs of 6-mil thickness were mounted on the support surface of the reagent holders as set forth in Example 1. The elevation of the discs were varied by increasing the thickness of the adhesive layer separating the underside of the disc from the support surface. The different discs were placed in the viewing housing of a type described above. The optical system of the fluorometer was focused to give a maximum signal at a 0.003-inch separation. As this separation increased, fluorescent signal decreased as shown in the following series of measurements.

| Approximate Separation Distance, inches | Fluorescent Signal, % of Maximum | |
| --- | --- | --- |
| | Series 1 | Series 2 |
| 0.003 | 100 | 100 |
| 0.010 | — | 99 |
| 0.017 | 95 | 92 |
| 0.024 | 79 | 77 |

What is claimed is:

1. A viewing housing for receiving a diagnostic reagent holder, said holder comprising an elongate shaft connected to a reagent containing surface and which is placed in a predetermined repeatable position in the housing, said viewing housing comprising housing wall means including a front wall portion, means defining a reagent holder slot in said housing, stop means for limiting penetration of the reagent holder a predetermined distance along said reagent holder slot defining means, and a reagent surface window opening through said front wall into said slot portion defining means for viewing the reagent containing surface when the reagent holder contacts said stop means.

2. A viewing housing as in claim 1 together with means for limiting lateral movement along said track means to define at least two precise predetermined lateral positions.

3. A viewing housing as in claim 1 together with a source of light and a receiver of excited light both aligned with said window.

4. A viewing housing as in claim 1 together with means defining a cuvette slot, with a cuvette viewing opening in said front wall portion laterally spaced from said reagent holder slot defining means.

5. A viewing housing as in claim 4 together with a base member adapted for stationary mounting to a detection assembly, and cooperating track means mounted to said viewing housing and base member for sliding lateral movement of said viewing housing.

6. A viewing housing as in claim 1 together with setting means for urging the reagent holder against a surface of said viewing housing when the holder contacts said stop means.

7. A viewing housing as in claim 6 in which said setting means urges said reagent holder toward said slot defining means, said setting means comprising a resiliently mounted setting member projecting toward said reagent holder.

8. A viewing housing as in claim 6 in which said reagent holder is disposed in said reagent holder slot defining means and in contact with said stop means and setting means with said reagent support surface visible in said window.

9. An elongate diagnostic reagent holder having front and rear sides and comprising an elongate shaft, mounting means coupled to said shaft, self-supporting film bearing a diagnostic reagent firmly retained toward the end of said shaft by said mounting means on said front side, said mounting means comprising means defining a retaining groove at one end of said shaft, said film being retained in registry with said retaining groove.

10. An elongate diagnostic reagent holder having front and rear sides and comprising an elongate shaft, mounting means coupled to said shaft, self-supporting film bearing a diagnostic reagent firmly retained toward the end of said shaft by said mounting means on said front side, and a locating means to assist registry thereof with a cooperating portion of a housing.

11. The holder of claim 10 in which said locating means comprises a recess and said cooperating housing portion comprises a projection.

12. The holder of claim 10 in which said locating means comprises a projection and said cooperating housing portion comprises a recess.

13. An elongate diagnostic reagent holder having front and rear sides and comprising an elongate shaft, mounting means coupled to said shaft, self-supporting film bearing a diagnostic reagent firmly retained toward the end of said shaft by said mounting means on said front side, and a pivot extension projecting from said holder at the film end and sufficiently aligned with said shaft to form a pivotal axis during stirring to facilitate liquid flow.

14. A continuous diagnostic reagent holder having front and rear sides and comprising an elongate shaft and a support surface adjacent one end of said shaft, a self-supporting film firmly adhered to the front side of said support surface, a diagnostic reagent coating affixed to said film, and protrusion means disposed externally adjacent the periphery of the film and projecting outwardly from the film a sufficient distance to protect the film from abrasion.

15. The holder of claim 14 in which said protrusion means comprises a protective rim around substantially all of the periphery of said film.

16. The holder of claim 14 together with an enlarged handle portion at the opposite end of the shaft from the film and of sufficient dimension transverse to the shaft to facilitate stirring a liquid with the holder and to support a sample identification label.

17. The holder of claim 14 in which said diagnostic reagent comprises a reagent selected from the group consisting of antigen or antibody.

18. The holder of claim 17 in which said antigen or antibody bears a fluorescent or phorphorescent label.

19. The holder of claim 14 in which said film comprises a disc bearing diagnostic reagent.

20. The holder of claim 19 in which said film is essentially impermeable to liquid.

21. The holder of claim 19 in which said diagnostic reagent is covalently attached to an external surface of the disc.

* * * * *